US009624150B2

(12) United States Patent
Nam et al.

(10) Patent No.: US 9,624,150 B2
(45) Date of Patent: Apr. 18, 2017

(54) METHOD OF PREPARING ALKANOL

(71) Applicant: LG CHEM, LTD., Seoul (KR)

(72) Inventors: Hyun Nam, Daejeon (KR); Jin Soo Kim, Daejeon (KR); Yong Jin Choe, Daejeon (KR); Sun Hyuk Choi, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 14/917,167

(22) PCT Filed: Sep. 17, 2014

(86) PCT No.: PCT/KR2014/008666
§ 371 (c)(1),
(2) Date: Mar. 7, 2016

(87) PCT Pub. No.: WO2015/041471
PCT Pub. Date: Mar. 26, 2015

(65) Prior Publication Data
US 2016/0207857 A1      Jul. 21, 2016

(30) Foreign Application Priority Data

Sep. 17, 2013   (KR) .................. 10-2013-0111558
Sep. 17, 2014   (KR) .................. 10-2014-0123680

(51) Int. Cl.
*C07C 29/141*    (2006.01)
*C07C 29/34*     (2006.01)
*C07C 29/14*     (2006.01)
*B01J 19/24*     (2006.01)

(52) U.S. Cl.
CPC ............. *C07C 29/141* (2013.01); *B01J 19/24* (2013.01); *C07C 29/14* (2013.01); *B01J 2219/24* (2013.01); *C07C 29/34* (2013.01)

(58) Field of Classification Search
CPC .................. C07C 29/141; C07C 29/34
See application file for complete search history.

(56) References Cited

U.S. PATENT DOCUMENTS

| 5,922,921 | A | 7/1999 | Unruh et al. |
| 2007/0287868 | A1 | 12/2007 | Arredondo et al. |
| 2012/0220806 | A1* | 8/2012 | Wick ............... C07C 29/34 568/905 |
| 2015/0166443 | A1* | 6/2015 | Arjona Antolin ....... C07C 29/34 568/902.2 |

FOREIGN PATENT DOCUMENTS

| CN | 1420959 A | | 5/2003 |
| JP | 2007-223947 A | | 9/2007 |
| JP | 2010-159212 A | | 7/2010 |
| KR | 10-2005-0000528 A | | 1/2005 |
| WO | WO91/04242 | * | 4/1991 |

OTHER PUBLICATIONS

Miller, R. et al. Ind. Eng. Chem., 1961, 53 (1), pp. 33-36.*
"Experimental Chemistry Lecture," 17 Organic compounds, vol. 2, Maruzen Publishing Co., Ltd., 1964, 2nd edition 2nd printing, pp. 96-99.
"Strategic Applications of Named Reactions in Organic Synthesis," Mar. 2007, 2nd printing, pp. 280-281.
Brieger, et al., "Catalytic Transfer Hydrogenation," Chemical Reviews, vol. 74, No. 5, 1974, pp. 567-580.
Harvey, et al., "Synthesis of renewable plasticizer alcohols by formal anti-Markovnikov hydration of terminal branched chain alkenes via borane-free oxidation/reduction sequence," Green Chem., vol. 14, 2012, pp. 2450-2456.
Mebane, et al., "Transfer Hydrogenation of Aldehydes With 2-Propanol and Raney® Nickel," Synthetic communications, vol. 35, No. 24, pp. 3083-3086 (2005).
Alonso, et al., "Nickel Nanoparticles in Hydrogen Transfer Reactions," Accounts of Chemical Research, vol. 44, No. 5, pp. 379-391 (2011).

* cited by examiner

*Primary Examiner* — Jafar Parsa
*Assistant Examiner* — Medhanit Bahta
(74) *Attorney, Agent, or Firm* — Dentons US LLP

(57) ABSTRACT

Provided are a method of preparing an alkanol and a device for preparing the same. According to the method and device, economic feasibility and stability of a preparation process may be enhanced, and mass production of an alkanol may be performed.

11 Claims, No Drawings

METHOD OF PREPARING ALKANOL

This application is a National Stage Entry of International Application No. PCT/KR2014/008666, filed Sep. 17, 2014, and claims the benefit of and priority to Korean Application No. 10-2013-0111558, filed Sep. 17, 2013 and Korean Application No. 10-2014-0123680, filed Sep. 17, 2014, all of which are incorporated herein by reference in their entirety for all purposes as if fully set forth herein.

TECHNICAL FIELD

The present application relates to a method of preparing an alkanol and a device for preparing the same.

BACKGROUND ART

Alkanols such as n-butanol are used in various applications as a solvent and an intermediate in chemical industries. For example, n-butanol is used as an ingredient in a solvent, butyl acetic acid, a medicine, a fragrance, a plasticizer, or a stabilizer.

In preparation of the alkanol, problems such as a process condition and a production cost are very important. For example, in a conventional process of preparing an alkanol, a hydrogenation process for reducing an aldehyde group using a high temperature and high pressure hydrogen gas is required, and thus high cost process equipment is needed, and there also is a problem in stability in the process.

Accordingly, a process of preparing an alkanol which can be more stable and reduce a process investment cost is required. In addition, to use the alkanol in various industrial fields, a process for mass production is required.

DISCLOSURE

Technical Problem

The present application is directed to providing a method of preparing an alkanol and a device for preparing the same.

Technical Solution

In one aspect, the present application provides a method of preparing an alkanol. According to the preparation method of the present application, an alkanol may be economically and stably prepared in a simpler process than the conventional method using a high pressure hydrogen gas. In one example, in the preparation method of the present application, a reaction of producing hydrogen and a process of producing an alkanol may be performed at the same time using a specific catalyst. For example, in the preparation process, secondary alcohols such as isopropyl alcohol and cyclohexanol are decomposed into acetone and hydrogen, and cyclohexanone and hydrogen respectively, using a raney nickel catalyst, thereby producing hydrogen, and the produced hydrogen may reduce an aldehyde group of n-butylaldehyde to prepare n-butanol. Accordingly, a problem such as a risk caused by the use of a conventional high pressure hydrogen gas in the process may be improved, and n-butanol may be economically prepared.

The method of preparing an alkanol according to the present application includes an operation of reacting a compound of Formula 1 and a compound of Formula 2.

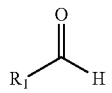

[Formula 1]

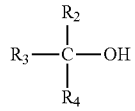

[Formula 2]

In Formula 1, $R_1$ is a linear, branched or cyclic alkyl group having 1 to 12 carbon atoms, or an alkenyl group having 1 to 12 carbon atoms. For example, $R_1$ may be an alkyl group having 1 to 10, 1 to 8, 1 to 6 or 1 to 4 carbon atoms, or an alkenyl group having 1 to 10, 1 to 8, 1 to 6 or 1 to 4 carbon atoms, and in one example, $R_1$ may be, but is not limited to, a methyl group, an ethyl group, a propyl group, a butyl group or a vinyl group.

In Formula 2, $R_2$, $R_3$ and $R_4$ are each independently hydrogen, an alkyl group having 1 to 12 carbon atoms, or an aryl group having 6 to 24 carbon atoms, and at least one of $R_2$, $R_3$ and $R_4$ is hydrogen. For example, when $R_2$ is hydrogen, $R_3$ and $R_4$ are each independently hydrogen, an alkyl group having 1 to 12 carbon atoms, for example, 1 to 10, 1 to 8, 1 to 6 or 1 to 4 carbon atoms, or an aryl group having 6 to 24, for example, 6 to 18 or 6 to 12 carbon atoms, and when $R_3$ is hydrogen, $R_2$ and $R_4$ may be hydrogen, an alkyl group having 1 to 12 carbon atoms, for example, 1 to 10, 1 to 8, 1 to 6, or 1 to 4 carbon atoms, or an aryl group having 6 to 24 carbon atoms, for example, 6 to 18 or 6 to 12 carbon atoms. In addition, when $R_4$ is hydrogen, $R_2$ and $R_3$ may be hydrogen, an alkyl group having 1 to 12 carbon atoms, for example, 1 to 10, 1 to 8, 1 to 6, or 1 to 4 carbon atoms or an aryl group having 6 to 24 carbon atoms, for example, 6 to 18 or 6 to 12 carbon atoms. Here, the alkyl group may be a linear, branched or cyclic alkyl group, but the present application is not limited thereto.

In one example, $R_2$ and $R_3$ are each independently hydrogen, an alkyl group having 1 to 12 carbon atoms or an aryl group having 6 to 24 carbon atoms, and in this case, at least one of $R_2$ and $R_3$ is hydrogen, and $R_4$ may be an alkyl group having 1 to 12 carbon atoms or an aryl group having 6 to 24 carbon atoms. For example, when $R_2$ is hydrogen, $R_3$ is hydrogen, an alkyl group having 1 to 12, for example, 1 to 10, 1 to 8, 1 to 6, or 1 to 4 carbon atoms, or an aryl group having 6 to 24, for example, 6 to 18, or 6 to 12 carbon atoms, and when $R_3$ is hydrogen, $R_2$ may be hydrogen, an alkyl group having 1 to 12, for example, 1 to 10, 1 to 8, 1 to 6, 1 to 4 carbon atoms, or an aryl group having 6 to 24, for example, 6 to 18 or 6 to 12 carbon atoms. The alkyl group having 1 to 12 carbon atoms may be, for example, a methyl group, an ethyl group, a propyl group or a butyl group, the aryl group having 6 to 24 carbon atoms may be, for example, a phenyl group, a tolyl group, a xylyl group or a naphthyl group, but the present application is not limited thereto. Accordingly, the compound of Formula 2 may be methanol, a primary alcohol or a secondary alcohol, for example, a primary alcohol or a secondary alcohol, and preferably, a secondary alcohol. When all of $R_2$ to $R_4$ are alkyl groups, the compound of Formula 2 is a tertiary alcohol, which may produce hydrogen in the presence of a metal catalyst. The reacting may be performed in the presence of a metal catalyst. The metal catalyst is used in the preparation method of the present application to increase reaction rates and reaction efficiencies of dehydrogenation for producing hydrogen by degrading the compound of Formula 2 and reduction of an aldehyde using the produced hydrogen.

In one example, the metal catalyst may be at least one selected from the group consisting of copper, cobalt, molybdenum, nickel, a nickel-aluminum alloy, a nickel-molybdenum alloy, raney cobalt, raney nickel, and a zinc-chromium alloy, and preferably, raney nickel.

The raney nickel catalyst has excellent substrate specificity or catalytic specificity, particularly, to a secondary alcohol. The "substrate specificity" or "catalytic specificity" refers to an effect of catalytic activity by a specific compound. For example, in the method of preparing an alkanol, as the compound of Formula 2, a secondary alcohol is used, and when raney nickel is used as the metal catalyst, an effect of stimulating the dehydrogenation of the compound of Formula 2 and the reduction of the compound of Formula 1 may be maximized, and an alkanol may be prepared with a high conversion rate.

As long as satisfying Formula 1, the compound of Formula 1 is not particularly limited, and for example, in Formula 1, $R_1$ may be an alkyl group having 2 to 6 carbon atoms, or an alkenyl group having 4 to 10 carbon atoms. The compound of Formula 1 may be, for example, n-butylaldehyde or 2-ethyl-2-hexenal.

As long as satisfying Formula 2, the compound of Formula 2 may be, but is not particularly limited to, for example, a primary alcohol or a secondary alcohol, and preferably, a secondary alcohol. When a tertiary alcohol is used, as described above, the tertiary alcohol may not produce hydrogen to reduce the compound of Formula 1 to an alkanol in the presence of a metal catalyst because of its molecular structure. In addition, the primary alcohol may produce hydrogen in the presence of a catalyst, but when the primary alcohol produces hydrogen, it is converted into an aldehyde compound such as the compound of Formula 1, and the aldehyde compound is reduced by hydrogen again, thereby producing a primary alcohol, and therefore, it may be difficult to provide hydrogen to the compound of Formula 1. However, the secondary alcohol produces hydrogen in the presence of a metal catalyst, particularly, a raney nickel catalyst, and is converted into a ketone compound which may be reduced by hydrogen in the presence of a raney nickel catalyst, and therefore hydrogen sufficient to reduce the compound of Formula 1 may be provided. Accordingly, when a secondary alcohol is used as the compound of Formula 2, an alkanol may be prepared with high efficiency.

In one example, the secondary alcohol may be a compound of Formula 3.

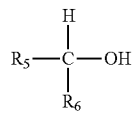

[Formula 3]

In Formula 3, $R_5$ and $R_6$ are each independently an alkyl group having 1 to 12 carbon atoms or an aryl group having 6 to 24 carbon atoms, or $R_5$ and $R_6$ may form a cycloalkyl group having 3 to 16 carbon atoms. In one example, $R_5$ and $R_6$ may be each independently an alkyl group having 1 to 10, 1 to 8, 1 to 6 or 1 to 4 carbon atoms, or an aryl group having 6 to 24, 6 to 18 or 6 to 12 carbon atoms, but is not limited to, for example, a methyl group, an ethyl group, a propyl group, a butyl group, a phenyl group, a tolyl group, a xylyl group or a naphthyl group. In addition, $R_5$ and $R_6$ may form a cycloalkyl group having 3 to 16 carbon atoms, for example, a cycloalkyl group having 4 to 12 or 5 to 8 carbon atoms, for example, a cyclohexyl group.

In one example, the compound of Formula 3 may include at least one compound selected from the group consisting of isopropyl alcohol, 2-butanol, 2-pentanol, 2-hexanol, 2-heptanol, glycerol, 3-methyl-2-butanol, α-phenylethanol, diphenylmethanol, 3-pentanol, 3,3-dimethyl-2-butanol, 4-phenyl-2-butanol, 1,2,3,4-tetrahydro-1-naphthol and cyclohexanol, and preferably, isopropyl alcohol, and/or cyclohexanol.

In one embodiment of the preparation method according to the present application, the reacting may include dehydrogenating in which the compound of Formula 2 is dehydrogenated in the presence of a metal catalyst, particularly, a raney nickel catalyst, and the dehydrogenating may include decomposing the compound of Formula 2 into a ketone compound and hydrogen in the presence of a raney nickel catalyst.

Here, the term "dehydrogenation" refers to a reaction of generating hydrogen by decomposing a compound including hydrogen, and for example, in the dehydrogenating, refers to decomposing the compound of Formula 2, that is, the secondary alcohol, into a ketone compound and hydrogen in the presence of a metal catalyst.

In one example, the ketone compound formed in the dehydrogenating may include at least one selected from the group consisting of acetone, cyclohexanone, butanone, 2-pentanone, 2-hexanone, 2-heptanone, dihydroxyacetone, methylisopropylketone, acetophenone, benzophenone, 3-pentanone, 3,3-dimethyl-2-butanone, 4-phenyl-2-butanone and tetralone, and when the compound of Formula 2 is isopropyl alcohol and/or cyclohexanol, the ketone compound may be acetone and/or cyclohexanone.

The preparation method of the present application may further include a reducing the compound of Formula 1 by hydrogen produced by the decomposition of the compound of Formula 2. The reducing is a step of reducing the compound of Formula 1 by inducing the reduction reaction of the compound of Formula 1 by hydrogen produced by the decomposition of the compound of Formula 2 in the dehydrogenating of the reacting, and therefore, the compound of Formula 1 is reduced, thereby producing an alkanol. The reduction operation may be performed after the above-described dehydrogenating, and in addition, may be simultaneously performed with the above-described dehydrogenating. As described above, all of the dehydrogenating and reducing may be performed in the presence of a metal catalyst, particularly, a raney nickel catalyst. In this case, the metal catalyst may stimulate generation of hydrogen by decomposition of the compound of Formula 2 into a ketone compound and hydrogen, and the hydrogen decomposed from the compound of Formula 2 may stimulate a reaction of reducing the compound of Formula 1. In addition, as the metal catalyst is used, a reaction of generating hydrogen and a process of preparing an alkanol may be simultaneously performed, and thus economic feasibility and stability of the process may be enhanced.

The metal catalyst may be present in a content ranging from 50 to 500 parts by weight, for example, 100 to 450, 200 to 400 or 250 to 350 parts by weight with respect to 100 parts by weight of the compound of Formula 1. When the metal catalyst is present at the above range of content, an alkanol can be prepared with excellent efficiency. For example, when the metal catalyst is present at less than 50 parts by weight with respect to 100 parts by weight of the compound of Formula 1, a catalytic activity may be reduced and thus a reaction rate may be decreased, or a conversion rate or selectivity may be decreased. Meanwhile, when the metal catalyst is present at more than 500 parts by weight with respect to 100 parts by weight of the compound of Formula 1, a catalyst content is increased, and a purification process after the reaction may be difficult to perform, and catalytic activity efficiency with respect to a catalyst content may not be high.

In one example, the secondary alcohol used in the preparation method may be included in a range of 100 to 2000 parts by weight, for example, 300 to 1800, 500 to 1600, 700 to 1400, 900 to 1200 or 1000 to 1100 parts by weight with respect to 100 parts by weight of the compound of Formula 1. When a reaction weight of the secondary alcohol is less than 100 parts by weight, sufficient hydrogen may not be provided, and thus a yield of n-butanol may be reduced, and when a reaction weight of the secondary alcohol is more than 2000 parts by weight, a production cost may be increased due to an excessive amount used, and there may be a difficult problem in purification.

In another embodiment of the present application, the method of preparing an alkanol may be performed in the state in which the compound of Formula 1 and the compound of Formula 2 are dissolved in an organic solvent. As the organic solvent is further included with the compound of Formula 1 and the compound of Formula 2 as described above, the reactants such as the compound of Formula 1 and the compound of Formula 2 may be more easily mixed, and a concentration of the compound of Formula 2 may be optimized, thereby further enhancing reaction efficiency.

In one example, as the organic solvent, an alcohol-based compound, an aromatic compound, a hydrocarbon-based compound, a heterocyclic compound, or an ether-based compound may be used. For example, as the alcohol-based compound, a primary alcohol having 1 to 12 carbon atoms may be used, as the aromatic compound, benzene, toluene or xylene may be used, as the heterocyclic compound, tetrahydrofuran or 1,4-dioxane may be used, and as the ether-based compound, diethylether or methyl-t-butyl ether may be used.

In the method of preparing an alkanol according to the present application, an operation of reacting the compound of Formula 1 with the compound of Formula 2 may be performed in a range of 50 to 150° C., for example, 60 to 120° C., 65 to 100° C., 70 to 90° C. or 75 to 85° C. Accordingly, as the process temperature is adjusted in the above range, a higher reaction efficiency may be obtained in the operation of reacting the compound of Formula 1 and the compound of Formula 2. For example, when the reacting is performed at less than 50° C., the compound of Formula 1 and the compound of Formula 2 may not sufficiently react, thereby a reaction effect may be considerably decreased or an amount of an alkanol produced may be decreased. In addition, when the reaction temperature is more than 100° C., an unnecessary side effect occurs excessively, and thus a conversion rate into an alkanol or selectivity may be considerably reduced.

In the preparation method according to the present application, in the presence of a metal catalyst, particularly, a raney nickel catalyst, a secondary alcohol, particularly, isopropyl alcohol and/or cyclohexanol may be dehydogenated, thereby reducing an aldehyde compound such as n-butylaldehyde to an alkanol such as n-butanol due to hydrogen produced by the dehydrogenation of isopropyl alcohol and/or cyclohexanol. In addition, since a high pressure hydrogen gas is not separately included as a reactant as used in the conventional method, a risk in the reaction process may be low, and production process equipment may be simplified. In addition, according to the preparation method of the present application, economic feasibility of the process may be enhanced, and thus mass production of n-butanol can be performed.

In another aspect, the present application provides a device for preparing an alkanol to be used in the preparation method.

The device for preparing an alkanol according to the present application may include a reactor and a reactant supply device. In one example, the reactor may be charged with a metal catalyst, and the reactant supply device may be a device for providing the compound of Formula 1 and the compound of Formula 2 into the reactor.

[Formula 1]
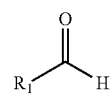

[Formula 2]
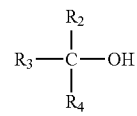

In Formulas 1 and 2, $R_1$ is a linear, branched or cyclic alkyl group having 1 to 12 carbon atoms, or an alkenyl group having 1 to 12 carbon atoms, $R_2$, $R_3$ and $R_4$ are each independently hydrogen, an alkyl group having 1 to 12 carbon atoms, or an aryl group having 6 to 24 carbon atoms, and at least one of $R_2$, $R_3$ and $R_4$ is hydrogen. Detailed descriptions of Compound 1 and Compound 2 are the same as described in the preparation method, and will be omitted below.

In one example, the reactor is a device for reacting the compound of Formula 1 and the compound of Formula 2, and the compound of Formula 1 and the compound of Formula 2 may be introduced into the reactor. In addition, the reactor may be charged with a metal catalyst, and the compound of Formula 1 and the compound of Formula 2 may be maintained under a suitable condition for performing a reaction. A type of the reactor included in the preparation device is not particularly limited, as long as any reactor is conventionally used in synthesis of a compound, and a size, shape and type of the reactor may be determined in consideration of a reaction condition, and amounts of a reactant and a product, and for example, a three necked flask equipped with a freezer and a stirrer may be used.

In one embodiment of the device for preparing an alkanol according to the present application, the compound of Formula 1 and the compound of Formula 2 may be provided into the reactor through the reactant supply device, and the reactor may be charged with a metal catalyst.

In this case, the compound of Formula 1 and the compound of Formula 2 may be reacted in the presence of the metal catalyst, and the compound of Formula 2 may be dehydrogenated to be decomposed into a ketone compound and hydrogen. In addition, the hydrogen produced by the decomposition of the compound of Formula 2 may reduce the compound of Formula 1, thereby preparing an alkanol. In one example, the metal catalyst charged into the reactor may be raney nickel, and in this case, dehydrogenation and reduction may easily occur in the operation of reacting the compound of Formula 1 and the compound of Formula 2, thereby preparing an alkanol with a high conversion rate. A detailed description of the above process is the same as that described in the above-described method of preparing an alkanol, and will be omitted below.

In one example, the compound of Formula 1 is not particularly limited as long as it satisfies Formula 1, and for example, in Formula 1, $R_1$ may be an alkyl group having 2 to 6 carbon atoms or an alkenyl group having 4 to 10 carbon atoms, and preferably, n-butyl aldehyde or 2-ethyl-2-hexenal.

In addition, the compound of Formula 2 is not particularly limited as long as it satisfies Formula 2, and for example, may be a secondary alcohol. In one example, the secondary alcohol may be a compound of Formula 3.

[Formula 3]

In Formula 3, $R_5$ and $R_6$ are each independently an alkyl group having 1 to 12 carbon atoms or an aryl group having 6 to 24 carbon atoms, or $R_5$ and $R_6$ may form a cycloalkyl group having 3 to 16 carbon atoms. A detailed description of Formula 3 is the same as described in the above-described preparation method, and will be omitted below.

In one example, the compound of Formula 3 may include at least one compound selected from the group consisting of isopropyl alcohol, 2-butanol, 2-pentanol, 2-hexanol, 2-heptanol, glycerol, 3-methyl-2-butanol, α-phenylethanol, diphenylmethanol, 3-pentanol, 3,3-dimethyl-2-butanol, 4-phenyl-2-butanol, 1,2,3,4-tetrahydro-1-naphthol and cyclohexanol, and preferably, isopropyl alcohol and/or cyclohexanol.

According to the preparation method and device of the present application, high purity n-butanol may be prepared with a high conversion rate, and a high pressure hydrogen gas is not used as a reaction material, and therefore economic feasibility and stability of the process may be enhanced.

Advantageous Effects

According to a preparation method and device of the present application, process economic feasibility and stability can be enhanced, and mass production of an alkanol can be performed.

MODE FOR INVENTION

Hereinafter, the present invention will be described in detail with reference to examples according to the present invention and comparative examples not according to the present invention, but the scope of the present invention is not limited to the following examples.

Example 1

2.0 g of n-butylaldehyde, 39.3 g of isopropyl alcohol and 6.0 g of raney nickel were placed into a 100 ml three necked flask equipped with a freezer and a stirrer, a temperature in the flask was increased to 80° C., and a reaction was performed for 3 hours. A mixture produced after the reaction was analyzed by GC, and it was confirmed that a conversion rate was 100%, and the mixture was composed of 3% acetone, 74% isopropyl alcohol, and 23% n-butanol (GC % area).

Example 2

2.0 g of n-butylaldehyde, 48.1 g of cyclohexanol and 6.0 g of raney nickel were placed into a 100 ml three necked flask equipped with a freezer and a stirrer, a temperature in the flask was increased to 86° C., and a reaction was performed for 3 hours. A mixture of a product produced after the reaction and a reactant remaining in the flask was analyzed by GC, and it was confirmed that a conversion rate was 100%, and the mixture was composed of 2% n-butanol, 97% cyclohexanol, and 1% cyclohexanone (GC % area).

Example 3

2.0 g of n-butylaldehyde, 39.3 g of isopropyl alcohol, 24.1 g of cyclohexanol and 6.0 g of raney nickel were placed into a 100 ml three necked flask equipped with a freezer and a stirrer, a temperature in the flask was increased to 75° C., and a reaction was performed for 3.5 hours. A mixture of a product produced after the reaction and a reactant remaining in the flask was analyzed by GC, and it was confirmed that a conversion rate was 100%, and the mixture was composed of 2% acetone, 56% isopropyl alcohol, 2% n-butanol, 39% cyclohexanol, and 1% cyclohexanone (GC % area).

Example 4

2.0 g of n-butylaldehyde, 21.8 g of toluene, 19.7 g of isopropyl alcohol and 6.0 g of raney nickel were placed into a 100 ml three necked flask equipped with a freezer and a stirrer, a temperature in the flask was increased to 74° C., and a reaction was performed for 3.5 hours. A mixture of a product produced after the reaction and a reactant remaining in the flask was analyzed by GC, and it was confirmed that a conversion rate was 100%, and the mixture was composed of 1% acetone, 27% isopropyl alcohol, 3% n-butanol, and 69% toluene (GC % area).

Example 5

2.0 g of n-butylaldehyde, 43.5 g of toluene, 24.1 g of cyclohexanol and 6.0 g of raney nickel were placed into a 100 ml three necked flask equipped with a freezer and a stirrer, a temperature in the flask was increased to 100° C., and a reaction was performed for 3 hours. A mixture of a product produced after the reaction and a reactant remaining in the flask was analyzed by GC, and it was confirmed that a conversion rate was 100%, and the mixture was composed of 1% n-butanol, 76% toluene, 22% cyclohexanol and 1% cyclohexanone (GC % area).

Example 6

2.0 g of n-butylaldehyde, 26.1 g of toluene, 7.9 g of isopropyl alcohol, 9.6 g of cyclohexanol and 6.0 g of raney nickel were placed into a 100 ml three necked flask equipped with a freezer and a stirrer, a temperature in the flask was increased to 79° C., and a reaction was performed for 4 hours. A mixture of a product produced after the reaction and a reactant remaining in the flask was analyzed by GC, and it was confirmed that a conversion rate was 100%, and the mixture was composed of 6% acetone and isopropyl alcohol, 3% n-butanol, 67% toluene, 23% cyclohexanol, and 1% cyclohexanone (GC % area).

Example 7

2.0 g of 2-ethyl-2-hexenal, 39.3 g of isopropyl alcohol, and 6.0 g of raney nickel were placed into a 100 ml three necked flask equipped with a freezer and a stirrer, a temperature in the flask was increased to 80° C., and a reaction was performed for 2 hours. A mixture of a product produced after the reaction and a reactant remaining in the flask was analyzed by GC, and it was confirmed that a conversion rate was 100%, and the mixture was composed of 2% acetone, 71% isopropyl alcohol, and 27% 2-ethyl hexanol (GC % area).

Comparative Example 1

2.0 g of n-butylaldehyde, 39.3 g of isopropyl alcohol, and 0.05 g of palladium on carbon (Pd/C) catalyst were placed into a 100 ml three necked flask equipped with a freezer and a stirrer, a temperature in the flask was increased to 76° C., and a reaction was performed for 4 hours. A mixture of a product produced after the reaction and a reactant remaining in the flask was analyzed by GC, and it was confirmed that production of n-butanol was not observed.

Comparative Example 2

2.0 g of n-butylaldehyde, 19.7 g of isopropyl alcohol, and 0.05 g of an Ni/SiO$_2$—Al$_2$O$_3$ catalyst were placed into a 100 ml three necked flask equipped with a freezer and a stirrer, a temperature in the flask was increased to 76° C., and a reaction was performed for 3.5 hours. A mixture of a product produced after the reaction and a reactant remaining in the flask was analyzed by GC, and it was confirmed that production of n-butanol was not observed.

In the method of preparing n-butanol according to an embodiment of the present application, n-butanol may be produced without using a high pressure hydrogen gas at a reaction condition of approximately 70 to 100° C., and particularly, as described in Example 1, it can be confirmed that when a process temperature and a content of the compound are suitably adjusted, n-butanol can be prepared with a very high conversion rate.

Meanwhile, as described in Comparative Examples 1 and 2, when a catalyst, other than a raney nickel catalyst, is used, it can be confirmed that n-butanol is not produced.

The invention claimed is:
1. A method of preparing an alkanol, comprising:
reacting a compound of Formula 1 with a compound of Formula 2 in the presence of a raney nickel, wherein the raney nickel is present at a content ranging from 50 to 500 parts by weight with respect to 100 parts by weight of the compound of Formula 1 and
wherein the compound of Formula 2 is a secondary alcohol:

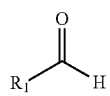
[Formula 1]

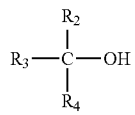
[Formula 2]

wherein R$_1$ is an alkyl group having 1 to 12 carbon atoms, or an alkenyl group having 1 to 12 carbon atoms, R$_2$, R$_3$ and R$_4$ are each independently hydrogen, an alkyl group having 1 to 12 carbon atoms, or an aryl group having 6 to 24 carbon atoms, and at least one of R$_2$, R$_3$ and R$_4$ is hydrogen.

2. The method according to claim 1, wherein R$_1$ of Formula 1 is an alkyl group having 2 to 6 carbon atoms or an alkenyl group having 4 to 10 carbon atoms.

3. The method according to claim 1, wherein the secondary alcohol is a compound of Formula 3:

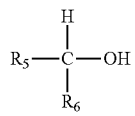
[Formula 3]

wherein R$_5$ and R$_6$ are each independently an alkyl group having 1 to 12 carbon atoms or an aryl group having 6 to 24 carbon atoms, or R$_5$ and R$_6$ form a cycloalkyl group having 3 to 16 carbon atoms.

4. The method according to claim 3, wherein the compound of Formula 3 includes at least one compound selected from the group consisting of isopropyl alcohol, 2-butanol, 2-pentanol, 2-hexanol, 2-heptanol, glycerol, 3-methyl-2-butanol, α-phenylethanol, diphenylmethanol, 3-pentanol, 3,3-dimethyl-2-butanol, 4-phenyl-2-butanol, 1,2,3,4-tetrahydro-1-naphthol and cyclohexanol.

5. The method according to claim 1, wherein the reacting includes dehydrogenating in which the compound of Formula 2 is dehydrogenated in the presence of raney nickel.

6. The method according to claim 5, wherein the dehydrogenating includes decomposition of the compound of Formula 2 into a ketone compound and hydrogen in the presence of raney nickel.

7. The method according to claim 6, wherein the ketone compound includes at least one compound selected from the group consisting of acetone, cyclohexanone, butanone, 2-pentanone, 2-hexanone, 2-heptanone, dihydroxyacetone, methylisopropylketone, acetophenone, benzophenone, 3-pentanone, 3,3-dimethyl-2-butanone, 4-phenyl-2-butanone and tetralone.

8. The method according to claim 6, further comprising:
reducing the compound of Formula 1 by hydrogen produced by the decomposition of the compound of Formula 2.

9. The method according to claim 1, wherein 100 to 2000 parts by weight of the secondary alcohol is reacted with respect to 100 parts by weight of the compound of Formula 1.

10. The method according to claim 1, wherein the reacting is performed in a state in which the compound of Formula 1 and the compound of Formula 2 are dissolved in an organic solvent.

11. A method according to claim 1, wherein the reacting is performed at a temperature ranging from 50 to 150° C.

* * * * *